(12) United States Patent
Huh et al.

(10) Patent No.: US 7,695,910 B2
(45) Date of Patent: Apr. 13, 2010

(54) METHOD FOR MANUFACTURING HYDROGEL BIOCHIP BY USING STAR-LIKE POLYETHYLENE GLYCOL DERIVATIVE HAVING EPOXY GROUP

(75) Inventors: Nam Huh, Seoul (KR); Mi-jung Song, Daejeon (KR); Jong-myeon Park, Daejeon (KR); Ga-young Park, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 648 days.

(21) Appl. No.: 11/510,931

(22) Filed: Aug. 28, 2006

(65) Prior Publication Data

US 2007/0020676 A1 Jan. 25, 2007

Related U.S. Application Data

(62) Division of application No. 10/231,829, filed on Aug. 30, 2002, now abandoned.

(30) Foreign Application Priority Data

Sep. 1, 2001 (KR) ................. 2001-53687
Aug. 14, 2002 (KR) ................. 2002-48128

(51) Int. Cl.
*C12Q 1/68* (2006.01)
*C12M 1/36* (2006.01)
*G01N 33/543* (2006.01)

(52) U.S. Cl. ............... 435/6; 435/283.1; 435/287.2; 436/518

(58) Field of Classification Search .............. None
See application file for complete search history.

(56) References Cited

U.S. PATENT DOCUMENTS 5,198,493 A * 3/1993 Holmberg et al. ........ 525/54.1
5,552,270 A 9/1996 Khrapko et al. ............ 435/6
5,554,744 A * 9/1996 Bhongle et al. .......... 536/25.3
5,736,257 A 4/1998 Conrad et al. ........... 428/474.4
5,741,700 A 4/1998 Ershov et al. ........... 435/287.1
5,744,305 A 4/1998 Fodor et al. .............. 435/6
5,770,721 A 6/1998 Ershov et al. ........... 536/25.3
5,847,019 A 12/1998 Conrad et al. ............ 522/2
6,046,305 A 4/2000 Choi ..................... 528/491
6,174,683 B1 * 1/2001 Hahn et al. ............... 435/6
6,762,019 B2 7/2004 Swan et al. ............... 435/6
2002/0064546 A1 5/2002 Harris ................... 424/426
2004/0023413 A1 2/2004 Opalsky ................. 436/518

FOREIGN PATENT DOCUMENTS

| JP | 61-189300 | 8/1986 |
|---|---|---|
| JP | 61-226059 | 10/1986 |
| JP | 2001-136972 | 5/2001 |
| WO | WO 91/12886 | 9/1991 |
| WO | WO 93/25247 | 12/1993 |
| WO | WO 97/39041 | 10/1997 |
| WO | WO 98/32790 | 7/1998 |
| WO | WO 00/02899 | 1/2000 |
| WO | WO 00/65097 | 11/2000 |
| WO | WO 01/09607 | 2/2001 |

* cited by examiner

*Primary Examiner*—B J Forman
(74) *Attorney, Agent, or Firm*—Cantor Colburn LLP (57) ABSTRACT

A method for manufacturing a biochip and a biochip manufactured by the method are provided. In the biochip manufacturing method, a star-like polyethylene glycol derivative having an epoxy group at its terminal is reacted with a low molecular weight hydrophilic polymer to form a matrix, and a probe is covalently bound to the matrix and immobilized on a solid substrate. The biochip has a 3-dimensional structure where it spatially protrudes from its surface and improved chip sensitivity. In addition, the biochip can be conveniently and efficiently manufactured using an aqueous solution at low costs.

13 Claims, 3 Drawing Sheets

SEQUENCE LISTING

```
<160> NUMBER OF SEQ ID NOS: 35

<210> SEQ ID NO 1
<211> LENGTH: 15
<212> TYPE: DNA
<213> ORGANISM: Homo sapiens

<400> SEQUENCE: 1
tgaactttgg acttc                                                   15

<210> SEQ ID NO 2
<211> LENGTH: 15
<212> TYPE: DNA
<213> ORGANISM: Homo sapiens

<400> SEQUENCE: 2
tgaacttggg acttc                                                   15

<210> SEQ ID NO 3
<211> LENGTH: 15
<212> TYPE: DNA
```

<213> ORGANISM: Homo sapiens

<400> SEQUENCE: 3
gttttggggg ggcag                                                    15

<210> SEQ ID NO 4
<211> LENGTH: 15
<212> TYPE: DNA
<213> ORGANISM: Homo sapiens

<400> SEQUENCE: 4
gttttggcgg ggcag                                                    15

<210> SEQ ID NO 5
<211> LENGTH: 15
<212> TYPE: DNA
<213> ORGANISM: Homo sapiens

<400> SEQUENCE: 5
tgcagctggc tcagt                                                    15

<210> SEQ ID NO 6
<211> LENGTH: 15
<212> TYPE: DNA
<213> ORGANISM: Homo sapiens

<400> SEQUENCE: 6
tgcagctagc tcagt                                                    15

<210> SEQ ID NO 7
<211> LENGTH: 15
<212> TYPE: DNA
<213> ORGANISM: Homo sapiens

<400> SEQUENCE: 7
gcactgggtg agccg                                                    15

<210> SEQ ID NO 8
<211> LENGTH: 15
<212> TYPE: DNA
<213> ORGANISM: Homo sapiens

<400> SEQUENCE: 8
gcactggatg agccg                                                    15

<210> SEQ ID NO 9
<211> LENGTH: 15
<212> TYPE: DNA
<213> ORGANISM: Homo sapiens

<400> SEQUENCE: 9 caaggggag tcctg                                                     15

<210> SEQ ID NO 10
<211> LENGTH: 15
<212> TYPE: DNA
<213> ORGANISM: Homo sapiens

<400> SEQUENCE: 10
caaggggaag tcctg                                                    15

<210> SEQ ID NO 11
<211> LENGTH: 15

```
<212> TYPE: DNA
<213> ORGANISM: Homo sapiens

<400> SEQUENCE: 11
cggtcgaggg gagct                                                15

<210> SEQ ID NO 12
<211> LENGTH: 15
<212> TYPE: DNA
<213> ORGANISM: Homo sapiens

<400> SEQUENCE: 12
ggcggtcgag ctggc                                                15

<210> SEQ ID NO 13
<211> LENGTH: 15
<212> TYPE: DNA
<213> ORGANISM: Homo sapiens

<400> SEQUENCE: 13
accatcttcg ccaca                                                15

<210> SEQ ID NO 14
<211> LENGTH: 15
<212> TYPE: DNA
<213> ORGANISM: Homo sapiens

<400> SEQUENCE: 14
accatctccg ccaca                                                15

<210> SEQ ID NO 15
<211> LENGTH: 15
<212> TYPE: DNA
<213> ORGANISM: Homo sapiens

<400> SEQUENCE: 15
cacaacatcc cacag                                                15

<210> SEQ ID NO 16
<211> LENGTH: 15
<212> TYPE: DNA
<213> ORGANISM: Homo sapiens

<400> SEQUENCE: 16
cacaacaacc cacag                                                15

<210> SEQ ID NO 17
<211> LENGTH: 15
<212> TYPE: DNA
<213> ORGANISM: Homo sapiens

<400> SEQUENCE: 17
gcgggccgcc ctgta                                                15

<210> SEQ ID NO 18
<211> LENGTH: 15
<212> TYPE: DNA
<213> ORGANISM: Homo sapiens

<400> SEQUENCE: 18
gcgggccacc ctgta                                                15

<210> SEQ ID NO 19
```

```
<211> LENGTH: 15
<212> TYPE: DNA
<213> ORGANISM: Homo sapiens

<400> SEQUENCE: 19
acctctcgct gcttg                                                          15

<210> SEQ ID NO 20
<211> LENGTH: 15
<212> TYPE: DNA
<213> ORGANISM: Homo sapiens

<400> SEQUENCE: 20
acctctcact gcttg                                                          15

<210> SEQ ID NO 21
<211> LENGTH: 15
<212> TYPE: DNA
<213> ORGANISM: Homo sapiens

<400> SEQUENCE: 21
aaggggcgga ggaac                                                          15

<210> SEQ ID NO 22
<211> LENGTH: 15
<212> TYPE: DNA
<213> ORGANISM: Homo sapiens

<400> SEQUENCE: 22
aaggggcaga ggaac                                                          15

<210> SEQ ID NO 23
<211> LENGTH: 15
<212> TYPE: DNA
<213> ORGANISM: Homo sapiens

<400> SEQUENCE: 23
gaggaaccgt ttcaa                                                          15

<210> SEQ ID NO 24
<211> LENGTH: 15
<212> TYPE: DNA
<213> ORGANISM: Homo sapiens

<400> SEQUENCE: 24
gaggaactgt ttcaa                                                          15

<210> SEQ ID NO 25
<211> LENGTH: 15
<212> TYPE: DNA
<213> ORGANISM: Homo sapiens

<400> SEQUENCE: 25
cacctccgtg acgag                                                          15

<210> SEQ ID NO 26
<211> LENGTH: 15
<212> TYPE: DNA
<213> ORGANISM: Homo sapiens

<400> SEQUENCE: 26
cacctccatg acgag                                                          15
```

```
<210> SEQ ID NO 27
<211> LENGTH: 15
<212> TYPE: DNA
<213> ORGANISM: Homo sapiens

<400> SEQUENCE: 27
tagacacgca cctcc                                                    15

<210> SEQ ID NO 28
<211> LENGTH: 15
<212> TYPE: DNA
<213> ORGANISM: Homo sapiens

<400> SEQUENCE: 28
tagacacaca cctcc                                                    15

<210> SEQ ID NO 29
<211> LENGTH: 15
<212> TYPE: DNA
<213> ORGANISM: Homo sapiens

<400> SEQUENCE: 29
caaccggcgc aaaga                                                    15

<210> SEQ ID NO 30
<211> LENGTH: 15
<212> TYPE: DNA
<213> ORGANISM: Homo sapiens

<400> SEQUENCE: 30
caaccggtgc aaaga                                                    15

<210> SEQ ID NO 31
<211> LENGTH: 15
<212> TYPE: DNA
<213> ORGANISM: Homo sapiens

<400> SEQUENCE: 31
cctgagatgc cggcg                                                    15

<210> SEQ ID NO 32
<211> LENGTH: 15
<212> TYPE: DNA
<213> ORGANISM: Homo sapiens

<400> SEQUENCE: 32
cctgagattg ccggc                                                    15

<210> SEQ ID NO 33
<211> LENGTH: 15
<212> TYPE: DNA
<213> ORGANISM: Homo sapiens

<400> SEQUENCE: 33
tggcgctgag ccggt                                                    15

<210> SEQ ID NO 34
<211> LENGTH: 15
<212> TYPE: DNA
<213> ORGANISM: Homo sapiens

<400> SEQUENCE: 34
tggcgctgag agccg                                                    15
```

```
<210> SEQ ID NO 35
<211> LENGTH: 15
<212> TYPE: DNA
<213> ORGANISM: Homo sapiens

<400> SEQUENCE: 35
tgttctcttg tcttg                                                    15
```

METHOD FOR MANUFACTURING HYDROGEL BIOCHIP BY USING STAR-LIKE POLYETHYLENE GLYCOL DERIVATIVE HAVING EPOXY GROUP

This application is a division of U.S. patent application Ser. No. 10/231,829, filed Aug. 30, 2002, now abandoned which claims foreign priority to Korean Patent Application No. 2001-53687 filed on Sep. 1, 2001 and Korean Patent Application No. 2002-48128 filed on Aug. 14, 2002, all of which are incorporated in their entirety by reference herein.

TECHNICAL FIELD

The present invention relates to a method for manufacturing a biochip, and more particularly, to a method for manufacturing a biochip by using a gel matrix.

BACKGROUND ART

The completion of the human genome project has greatly increased the need for an efficient method for providing a large quantity of genetic information necessary for genetic disease diagnosis, treatment, and prevention. Despite the development of DNA polymerase chain reaction (PCR) and its automation, Sanger's method for nucleotide sequencing is still burdensome and delicate to handle, and needs lots of time, effort, and cost. Thus, there have been many attempts to find a new nucleotide sequencing system capable of analyzing a large number of genes.

A DNA chip refers to a microarray of less than 1 square inch, which is formed by immobilizing oligonucleotide probes, each probe including a few to hundreds of nucleotides, at hundreds to hundreds of thousands of appropriate positions on a solid surface made of silicon, surface-modified glass, polypropylene, or activated polyacrylamide. As a target DNA fragment is bound to the DNA chip, the target DNA fragment complementarily hybridizes to the oligonucleotide probes immobilized on the DNA chip. The hybridization is optically or radiochemically observed and analyzed to identify the nucleotide sequence of the target DNA.

Use of the DNA chip reduces the size of a DNA assay system and enables genetic assay with a trace of a sample. In addition, multiple sequences of a target DNA can be simultaneously assayed, thereby conveniently and rapidly providing the genetic information of the target DNA at low costs. The DNA chip can assay a large amount of genetic information and the relevancy of the genes within a short period of time. Accordingly, the DNA chip is expected to have wide applications, for example, to genetic disorder and cancer diagnosis, mutant and pathogen detection, gene expression assay, drug discovery, etc. In addition, the DNA chip can be used as a microorganism or pollutant detector to find out antidotal genes and further to produce antidotes on a large scale based on genetic recombination technologies. The DNA chip can lead to great improvements in most biological industries, including the production of medicinal crops or low-fat meat.

DNA chips are classified into an oligo-chip and a cDNA chip according to the type of probes immobilized thereon. According to the manufacturing method, DNA chips are classified into a lithography chip, a pin-type spotting chip, an ink-jet type spotting chip, and an electronic addressing DNA chip that electronically integrates DNA into a substrate.

The first generation DNA chip, a 2-dimensional (2D) chip in which oligonucleotides are attached to a substrate as a monolayer, causes a considerable error when the degree of hybridization is relatively compared, due to spot-to-spot variation of the probes attached to the substrate, and has low sensitivity, and thus needs an expensive confocal fluorescence microscope to detect the hybridized DNA. In addition, the surface of the solid substrate is treated with a mixture of an organic solvent and an aqueous solution to induce chemical reactions.

U.S. Pat. No. 5,744,305 discloses an example of the first generation DNA chip manufactured by photolithography using a photolabile protecting group. In the first generation DNA chip, various polymers such as peptides and oligonucleotides are arrayed on the substrate.

To address the drawbacks of the first generation DNA chip, the following second generation DNA chip was developed. U.S. Pat. Nos. 5,736,257 and 5,847,019 disclose methods for manufacturing biochips, in which a hydroxyl (OH) group on a substrate is treated with silane to form a molecular layer of a vinyl group on the substrate, and a network layer is formed on the molecular layer through polymerization of acrylamide and activated and patterned using light to bind the network layer to a biomaterial. In these methods, due to a 3-D gel network of the polyacrylamide formed on the molecular layer of the vinyl group, a quantitative variation of probes immobilized thereon is reduced, and chip sensitivity is improved. However, disadvantageously, the cost is high and a long assay period of time is required.

U.S. Pat. Nos. 5,552,270, 5,741,700, and 5,770,721 disclose DNA sequence assay methods using a second generation DNA chip including an oligonucleotide array matrix and a solid substrate. The matrix is bound to the solid substrate via a gel layer in a pattern of square dots spaced a constant distance from one another. In the manufacture of the DNA chip, a polyacrylamide gel is applied between two glass slides spaced about 30 μm apart. One glass slide having the size of 100×100×30 μm$^3$ is removed, and the remaining glass slide coated with the gel is dried and formed into a dot pattern by partially removing the gel through a mechanical tool or laser. The amide group of the gel layer is chemically transformed into reactive hydrazide form, and DNA probes having N-methyluridine at 5'-terminal are transformed into dialdehyde. The oligonucleotide probe is immobilized on the substrate in three dimensions by reacting the probe with the reactive gel.

The DNA chip is manufactured through multiple processes over a longer period of time of from 1 to 2 days, wherein each of the processes is followed by a thorough wash process. Accordingly, the assay yield is susceptible to reaction conditions, and irregular adsorption of the target DNA to the gel surface increases background noise.

WO 00/65097 and WO 00/2899 disclose 3-D DNA chips using a hydrogel having an isocyanate (NCO) group. The hydrogel is a hydrophilic network polymer which is glassy in a dehydrated state and swells to form a gel in the presence of water. According to the disclosures, the isocyanate group is known to be involved in covalent bonding between the hydrogel and probes as well as in polymerization of the hydrogel itself. A hydrogel having the isocyanate group, for example, polyethyleneoxide having an isocyanate group or a copolymer of polyethyleneoxide having an isocyanate group and polypropyleneoxide, and probes having an amino group at the 5'-terminal are mixed in an aqueous solution, and the probes are immobilized on the gel in three dimensions and reacted with an amino group on the glass surface to attach the probes on the substrate.

The isocyanate group is hydrolyzed too rapidly to control. To prevent the hydrolysis of the isocyanate group there is a need to manufacture a DNA chip at low temperature. As the isocyanate groups that neither covalently bind to the probes nor are involved in gel polymerization are hydrolyzed, the polymerization is accelerated to increase viscosity and to solidify a spotting pin. Also, generation of carbon dioxide makes spotting size control difficult.

DISCLOSURE OF THE INVENTION

It is an object of the present invention to provide an easy-to-manufacture hydrogel biochip having an improved sensitivity.

It is another object of the present invention to provide a method for manufacturing a biochip having an improved sensitivity.

The present invention provides a method for manufacturing a hydrogel biochip, comprising: mixing a star-like polyethylene glycol derivative having an epoxy group at its terminal, a hydrophilic polymeric cross-linking agent and a probe in a aqueous solution to form a mixture solution; and applying the mixture solution on a substrate to form a hydrogel such that the probe is immobilized to the substrate.

The method for manufacturing the hydrogel biochip according to the present invention may comprise forming a matrix of a star-like polyethylene glycol derivative having an epoxy group at its terminal and a hydrophilic polymeric cross-linking agent and reacting the matrix with a probe to form a matrix-probe conjugate.

The hydrogel biochip manufacturing method according to the present invention will be described in detail below.

Initially, a star-like polyethylene glycol is reacted with excess epichlorohydrine and sodium hydroxide to have an epoxy group to its terminal. Next, the matrix is formed by using a low molecular weight hydrophilic polymer, and preferably, having a hydrophilic hydroxy group, amino group, or thiol group, and having an average molecular weight of about 60-100,000 as a cross-linking agent. A probe having a nucleophilic group at its terminal is covalently bound to the matrix to form the matrix-probe conjugate. The formation of the matrix and the formation of the matrix-probe conjugate are sequentially or simultaneously performed. The term "probe" used throughout the specification means all substances specifically bound to a target substance and useful to measure the properties of the target substance through analysis of the binding between the probe and the target substance. Preferably, the probe includes nucleic acids, such as deoxyribonucleic acid (DNA), ribonucleic acid (RNA), and peptide nucleic acid (PNA), a protein, or an oligopeptide. The low molecular weight hydrophilic polymer used in the present invention includes polyethylene glycol having, for example, an average molecular weight of 60-100,000, polyethyleneamine, polypropyleneoxide and polyol. The term "star-like polyethylene glycol" used throughout the specification means a PEG derivative having branches oriented in 3 or more directions, thereby having a star-like form. Thus, the star-like PEG derivatives of the present invention can be cross-linked by a cross-linking agent and form a 3-dimensional polymer matrix.

According to the present invention, the matrix-probe conjugate is immobilized on a solid substrate, and preferably, whose surface is treated to expose an amide group, by microspotting to form the hydrogel biochip according to the present invention. Suitable materials for the solid substrate include glass, quartz, silicon, plastic, polypropylene, polycarbonate, and activated acrylamide, etc.

The method for manufacturing the hydrogel biochip according to the present invention includes preparing a mixture solution of a star-like polyethylene glycol having an epoxy group at its terminal, a hydrophilic cross-linking agent, and a probe, and immobilizing the mixture solution on substrate.

The immobilization is performed, for example, at a temperature of about 40-70° C. and a humidity of about 60-30%, and preferably, at 40° C. and 60%, 60° C. and 40%, or 70° C. and 30%. The spot pattern formed on the substrate as a result of the immobilization varies depending on the type of the cross-linking agent and reaction conditions such as mixing ratio, temperature, and humidity. In this particular embodiment of the present invention, the same polyethylene derivative, hydrophilic polymeric cross-linking agent, probe, and substrate as described above are applied.

The present invention provides a hydrogel biochip manufactured by the above-described hydrogel biochip manufacturing method. The hydrogel biochip according to the present invention comprises a solid substrate, a matrix covalently bound to the solid substrate as a reaction product between a star-like polyethylene glycol having an epoxy group at its terminal and a hydrophilic polymeric cross-linking agent, and probes covalently bound to the matrix.

The present invention also provides an assay method for detecting a binding between a probe and a target sample, comprising applying the target sample including a target substance to be bound to the probe to the hydrogel biochip manufactured by the method according to the present invention and detecting the target substance specifically bound to the probe. It is preferable to label the probe with a signaling substance, such as a fluorescent dye for easy detection of the target substance. The binding between a probe and a target substance can be detected by a variety of methods, for example, a fluorescent detection method, an electrochemical detection method, a mass detection method, a charge detection method, or an optical detection method, which are currently in wide use and are classified according to the type of the signaling substance labeled to the target substance.

BEST MODE FOR CARRYING OUT THE INVENTION

The present invention will be described in greater detail with reference to the following examples. The following examples are for illustrative purposes and are not intended to limit the scope of the invention.

Example 1

Synthesis of Star-Like Polyethylene Glycol Having Epoxy Group 7.5 mL of epichlorohydrine and 0.32 g of tetrabutylammonium bromide were added to 2 mL of NaOH solution (50% by weight) and stirred, and 1 g of pentaerythritol ethoxylate was slowly added to the mixture and stirred at room temperature for 18 hours. The completion of the reaction was identified by thin layer chromatography. When the reaction was not completed, the mixture was further stirred for 1 hour at 60° C. Next, the reaction product was diluted with an addition of 30 mL of water and extracted three times with 40 mL of methylene chloride. An organic solvent layer was washed three times with 40 mL of saturated NaHCO$_3$, and anhydrous MgSO$_4$ was added, and the solvent was removed at a low pressure. Next, the resultant product was dried in a vacuum for 2 days to remove the epichlorohydrine residue. The resultant star-like polyethylene glycol (PEG) derivative having an epoxy group was identified by H-NMR and titration of the epoxy group using 0.1 N HBr/glacial acetic acid.

Example 2

Synthesis of Diamine Cross-Linking Agent 5 g (9.2 mmol) of penta(ethylene glycol)di-tosylate was dissolved in 40 mL of DMF, and 4.2 g of (64.1 mmol) NaN$_3$ and 0.5 mL of pyridine were sequentially added to the solution and stirred at 140° C. for 18 hours. After removing the solvent at a low pressure, the resultant product was stirred with an addition of 200 mL of water and extracted with 100 mL of methylene chloride. An organic solvent layer was washed three times with 100 mL of brine, and anhydrous MgSO$_4$ was added, and the solvent was removed at a low pressure. Next, the resultant product was subjected to flash column chromatography (EA:nHex=1:2) to isolate a diazide intermediate product. The intermediate product was dissolved in 30 mL of methanol, and 10% Pd—C (0.1 equivalent) was added, followed by a reduction reaction for 18 hours using hydrogen gas. A catalyst was removed using a Celite pad, and the pad was washed with ethanol. The filtrate and the ethanol used to wash the pad were mixed, and the solvent was removed at a low pressure to obtain a diamine cross-linking agent.

Example 3

Preparation of Gel Matrix Solution Using Cross-Linking Agent (1) Preparation of Gel Matrix Solution Using Diamine Cross-Linking Agent 100 mg of the star-like PEG derivative having the epoxy group prepared in Example 1 was stirred with an addition of 4 mL water. 5.8 mg of the diamine cross-linking agent synthesized in Example 2 was added to the mixture and stirred at room temperature for 18 hours and stored in a liquid state at 4° C.

(2) Preparation of Gel Matrix Solution Using PEG as a Cross-Linking Agent

PEG having a molecular weight of 200, 400, 600, and 1,500 were separately dissolved in an aqueous solution of 2 N NaOH and stirred in an ice bath to obtain different PEG cross-linking agent solutions.

Next, a portion of the star-like PEG derivative having the epoxy group prepared in Example 1 was dissolved in a carbonate buffer solution (0.1 M, pH 9.1). The prepared PEG cross-linking solution was slowly added into the solution and stirred at room temperature for 3 hours. After the completion of the reaction, the reaction product was extracted with methylene chloride, and the solvent was removed at a low pressure and stored at 4° C.

For comparison, when a gel matrix solution was prepared using a PEG cross-linking solution having a molecular weight of 100,000, a solid reaction product was obtained. As a result of the gel permeation chromatography, the solid product was identified as a dimer having 5-6 epoxy groups, rather than the matrix material. Accordingly, it is evident that PEG having a molecular weight of less than 100,000 can be used as the cross-linking agent in the present invention.

Example 4

Manufacture of Biochip by Spotting Gel Matrix-DNA Conjugate Solution

To the gel matrix solution prepared in Example 3, oligonucleotide probes including the star-like PEG having the epoxy group, the cross-linking agent, and oligonucleotides in an equivalent ratio of 4:1:4 were added, stirred at 37° C., and left for 14 hours to obtain a spotting solution of a matrix-DNA conjugate.

The spotting solution was applied by spotting to a glass substrate whose surface had been treated to expose an amino group and left in a wet chamber at 37° C. for 4 hours. To prevent the target nucleic acid from adhering to an unnecessary portion on the glass surface, further reaction is performed such that amino groups at non-spotting positions on the glass substrate were negatively charged, which is an essential step for controlling background noise, and the resultant biochip was stored in a dryer.

Example 5

Chip Test

In the chip performance test, a full length of the wild type gene of hepatocyte nuclear factor-1α (HNF-1α) and a heterozygote mutant obtained by an insertion of nucleotide A immediately after (toward 3'-terminal) the $5613^{th}$ nucleotide of exon 9 of the HNF-1α amplified through multiplex polymerase chain reaction (PCR) were used as a target nucleotide to be hybridized to the probe. In the PCR of the target nucleotide, Cy3-dUTP was added to fluorescently label the target nucleotide.

The following oligonucleotides (SEQ ID Nos. 1 through 34) were used as probes.

For hybridization of the target nucleotide to the probes, 20 nM target nucleotide solution in 0.1% 6SSPET (Saline Sodium Phosphate EDTA buffer containing 0.1% Triton X-100) and a matrix-DNA conjugate were immobilized on the chip and reacted at 37° C. for 16 hours. The chip was washed at room temperature with 0.05% 6SSPET and 0.05% 3SSPET in sequence for 5 minutes each, air-dried at room temperature for 5 minutes, and scanned by a scanner (Exon Co., GenePix 4000B).

SEQ ID No. 1: tgaacttTggacttc—a probe complementary to HNF-1α gene promoter region, wherein T in the middle of the probe sequence is paired with the $432^{nd}$ base of the wild type promoter, and its side probe sequence perfectly matches the side sequence of the $432^{nd}$ base.

SEQ ID No. 2: tgaacttGggacttc—a probe complementary to a target nucleotide having a point mutation (A→C) at the $432^{nd}$ base of the wild type promoter.

SEQ ID No. 3: gttttggGggggcag—a probe complementary to HNF-1α gene promoter region, wherein G in the middle of the probe sequence is paired with the $592^{nd}$ base of the wild type promoter, and its side probe sequence perfectly matches the side sequence of the $592^{nd}$ base.

SEQ ID No. 4: gttttggCggggcag—a probe complementary to a target nucleotide having a point mutation (C→G) at the 592$^{nd}$ base of the wild type promoter.

SEQ ID No. 5: tgcagctGgctcagt—a probe complementary to HNF-1α gene exon 1 region, wherein G in the middle of the probe sequence is paired with the 733$^{rd}$ base of the wild type exon 1, and its side probe sequence perfectly matches the side sequence of the 733$^{rd}$ base of exon 1.

SEQ ID No. 6: tgcagctAgctcagt—a probe complementary to a target nucleotide having a point mutation (C→T) at the 733$^{rd}$ base of the wild type exon 1.

SEQ ID No. 7: gcactggGtgagccg—a probe complementary to HNF-1α gene exon 1 region, wherein G in the middle of the probe sequence is paired with the 806$^{th}$ base of the wild type exon 1, and its side probe sequence perfectly matches the side sequence of the 806$^{th}$ base of exon 1.

SEQ ID No. 8: gcactggAtgagccg—a probe complementary to a target nucleotide having a point mutation (C→T) at the 806$^{th}$ base of the wild type exon 1.

SEQ ID No. 9: caaggggGagtcctg—a probe complementary to HNF-1α gene exon 1 region, wherein G in the middle of the probe sequence is paired with the 856$^{th}$ base of the wild type exon 1, and its side probe sequence perfectly matches the side sequence of the 856$^{th}$ base of exon 1.

SEQ ID No. 10: caaggggAagtcctg—a probe complementary to a target nucleotide having a point mutation (C→T) at the 856$^{th}$ base of the wild type exon 1.

SEQ ID No. 11: cggtcgaGgggagct—a probe complementary to HNF-1α gene exon 1 region, wherein G in the middle of the probe sequence is paired with the 875$^{th}$ base of the wild type exon 1, and its side probe sequence perfectly matches the side sequence of the 875$^{th}$ base of exon 1.

SEQ ID No. 12: ggcggtcGagctggc—a probe complementary to a target nucleotide having a deletion mutation of 5 bases from the 875$^{th}$ to 879$^{th}$ bases of the wild type exon 1.

SEQ ID No. 13: accatctTcgccaca—a probe complementary to HNF-1α gene exon 2 region, wherein T in the middle of the probe sequence is paired with the 1778$^{th}$ base of the wild type exon 2, and its side probe sequence perfectly matches the side sequence of the 1778$^{th}$ base of exon 2.

SEQ ID No. 14: accatctCcgccaca—a probe complementary to a target nucleotide having a point mutation (A→G) at the 1778$^{th}$ base of the wild type exon 2.

SEQ ID No. 15: cacaacaTcccacag—a probe complementary to HNF-1α gene exon 2 region, wherein T in the middle of the probe sequence is paired with the 1812$^{th}$ base of the wild type exon 2, and its side probe sequence perfectly matches the side sequence of the 1812$^{th}$ base of exon 2.

SEQ ID No. 16: cacaacaAcccacag—a probe complementary to a target nucleotide having a point mutation (A→T) at the 1812$^{th}$ base of the wild type exon 2.

SEQ ID No. 17: gcgggccGccctgta—a probe complementary to HNF-1α gene exon 2 region, wherein G in the middle of the probe sequence is paired with the 1910$^{th}$ base of the wild type exon 2, and its side probe sequence perfectly matches the side sequence of the 1910$^{th}$ base of exon 2.

SEQ ID No. 18: gcgggccAccctgta—a probe complementary to a target nucleotide having a point mutation (C→T) at the 1910$^{th}$ base of the wild type exon 2.

SEQ ID No. 19: acctctcGctgcttg—a probe complementary to HNF-1α gene exon 2 region, wherein G in the middle of the probe sequence is paired with the 1940$^{th}$ base of the wild type exon 2, and its side probe sequence perfectly matches the side sequence of the 1940$^{th}$ base of exon 2.

SEQ ID No. 20: acctctcActgcttg—a probe complementary to a target nucleotide having a point mutation (C→T) at the 1940$^{th}$ base of the wild type exon 2.

SEQ ID No. 21: aaggggcGgaggaac—a probe complementary to HNF-1α gene exon 3 region, wherein G in the middle of the probe sequence is paired with the 2659$^{th}$ base of the wild type exon 3, and its side probe sequence perfectly matches the side sequence of the 2659$^{th}$ base of exon 3.

SEQ ID No. 22: aaggggcAgaggaac—a probe complementary to a target nucleotide having a point mutation (C→T) at the 2659$^{th}$ base of the wild type exon 3.

SEQ ID No. 23: gaggaacCgtttcaa—a probe complementary to HNF-1α gene exon 3 region, wherein C in the middle of the probe sequence is paired with the 2667$^{th}$ base of the wild type exon 3, and its side probe sequence perfectly matches the side sequence of the 2667$^{th}$ base of exon 3.

SEQ ID No. 24: gaggaacTgtttcaa—a probe complementary to a target nucleotide having a point mutation (G→A) at the 2667$^{th}$ base of the wild type exon 3.

SEQ ID No. 25: cacctccGtgacgag—a probe complementary to HNF-1α gene exon 4 region, wherein G in the middle of the probe sequence is paired with the 3297$^{th}$ base of the wild type exon 4, and its side probe sequence perfectly matches the side sequence of the 3297$^{th}$ base of exon 4.

SEQ ID No. 26: cacctccAtgacgag—a probe complementary to a target nucleotide having a point mutation (C→T) at the 3297$^{th}$ base of the wild type exon 4.

SEQ ID No. 27: tagacacGcacctcc—a probe complementary to HNF-1α gene exon 4 region, wherein G in the middle of the probe sequence is paired with the 3305$^{th}$ base of the wild type exon 4, and its side probe sequence perfectly matches the side sequence of the 3305$^{th}$ base of exon 4.

SEQ ID No. 28: tagacacAcacctcc—a probe complementary to a target nucleotide having a point mutation (C→T) at the 3305$^{th}$ base of the wild type exon 4.

SEQ ID No. 29: caaccggCgcaaaga—a probe complementary to HNF-1α gene exon 4 region, wherein C in the middle of the probe sequence is paired with the 3332$^{th}$ base of the wild type exon 4, and its side probe sequence perfectly matches the side sequence of the 3332$^{th}$ base of exon 4.

SEQ ID No. 30: caaccggTgcaaaga—a probe complementary to a target nucleotide having a point mutation (G→A) at the 3332$^{th}$ base of the wild type exon 4.

SEQ ID No. 31: cctgagaTgccggcg—a probe complementary to HNF-1α gene exon 9 region, wherein T in the middle of the probe sequence is paired with the 5613$^{th}$ base of the wild type exon 9, and its side probe sequence perfectly matches the side sequence of the 5613$^{th}$ base of exon 9.

SEQ ID No. 32: cctgagaTtgccggc—a probe complementary to a target nucleotide having an insertion mutation of base A immediately after the 5613$^{th}$ base of the wild type exon 9.

SEQ ID No. 33: tggcgctGagccggt—a probe complementary to HNF-1α gene exon 9 region, wherein G in the middle of the probe sequence is paired with the 5688$^{th}$ base of the wild type exon 9, and its side probe sequence perfectly matches the side sequence of the 5688$^{th}$ base of exon 9.

SEQ ID No. 34: tggcgctGagagccg—a probe complementary to a target nucleotide having an insertion mutation of bases T and C immediately after the 5688$^{th}$ base of the wild type exon 9.

Figure 1:
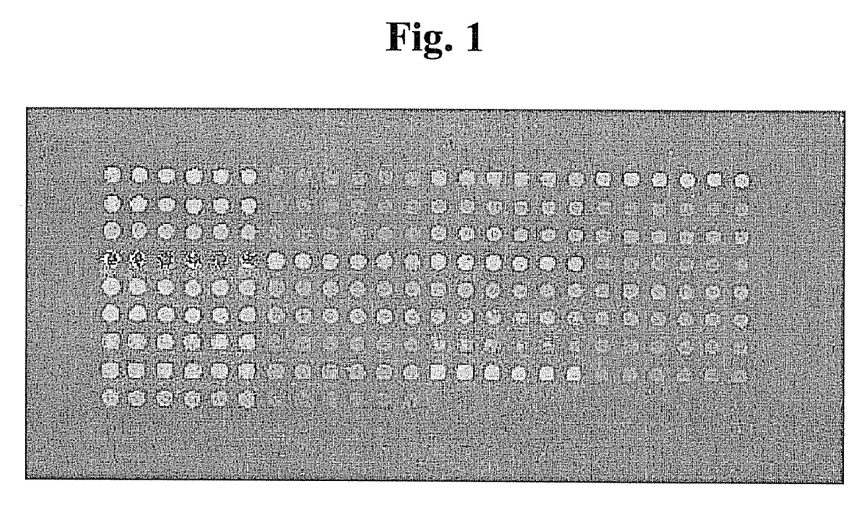
FIG. 1 is a photograph showing the result of hybridization when a full length of the wild type gene of hepatocyte nuclear factor-1α (HNF-1α) is used as a target nucleotide.
Figure 2:
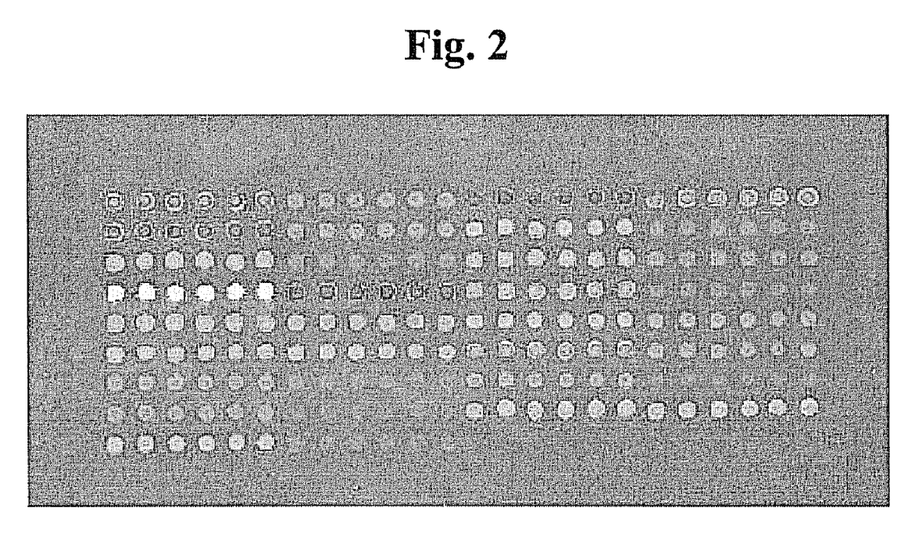
FIG. 2 is a photograph showing the result of hybridization when a heterozygote mutant obtained by an insertion of nucleotide A immediately after the $5613^{th}$ nucleotide of exon 9 of the HNF-1α gene is used as a target nucleotide.

The result of scanning after the hybridization reaction between the probes and the target nucleotide is shown in FIGS. 1 and 2. FIG. 1 is for the full length of the wild type gene of HNF-1α used as the target nucleotide. FIG. 2 is for the heterozygote mutant used as the target nucleotide, which was obtained by an insertion of nucleotide A immediately after the 5613$^{th}$ nucleotide of exon 9 region of the HNF-1α gene.

In FIGS. 1 and 2, 6 spots for each identical probe were spotted on the chip, from the left to the right in the uppermost line, probes of SEQ ID Nos. 1, 2, 3, and 4 were immobilized as spots. In the next line, probes of SEQ ID Nos. 5, 6, 7, and 8 were immobilized in the same manner. The remaining probes up to SEQ ID No. 34 were spotted on the chip in the same manner. Here, the spot size was 170±5 µm, and the spot interval was adjusted to be 375 µm.

A spot-to-spot variation in the identical probe group was 8%, and a chip-to-chip variation was 10.6%, when measured as a coefficient of variation (CV). Comparing to conventional 2D chips having a 25-30% coefficient of spot-to-spot variation, the 3D immobilization technique applied in the present invention is proved to be effective in reducing an error between probes. CV is expressed as a percentage of standard deviation to mean value.

As shown in FIG. 1, the immobilized spots of the wild type probes (i.e., SEQ ID Nos. 1, 3, 5, 7, 9, 11, 13, 15, 17, 19, 21, 23, 25, 27, 29, 31, and 33) showed a strong fluorescent intensity, compared with the immobilized spots of the mutant probes (i.e., SEQ ID Nos. 2, 4, 6, 8, 10, 12, 14, 16, 18, 20, 22, 24, 26, 28, 30, 32, and 34). Accordingly, the full length of the wild type gene of HNF-1α used as the target nucleotide is hybridized to the bases of the mutant-free wild type probes.

As shown in FIG. 2, a similar result as in FIG. 1 was observed for the immobilized spots of the wild type probes (i.e., SEQ ID Nos. 1, 3, 5, 7, 9, 11, 13, 15, 17, 19, 21, 23, 25, 27, 29, 31, and 33). However, the immobilized spot of the probe of SEQ ID No. 32, which is one of the mutant probes, showed a strong fluorescent intensity, unlike the result of FIG. 1. The insertion mutation of nucleotide A immediately after the 5613$^{th}$ nucleotide of the exon 9 region of the HNF-1α gene can be easily identified.

Example 6

Manufacture of Biochip Using Matrix Directly Formed on Substrate

According to the present invention, the matrix can be directly formed on a substrate as well as can be manufactured in a container separate from the substrate.

In a carbonate buffer solution (0.25 mM, pH 9.5) an oligonucleotide probe (5'-tgttctcttgtcttg-3': SEQ ID No. 35), the star-like polyethylene derivative having the epoxy group prepared in Example 1, and the diamine cross-linking agent prepared in Example 2 were mixed in a ratio of 1:8:8. The concentration of the oligonucleotide was adjusted not to exceed 400 µM. Next, the mixture solution was mixed with an equal volume of DMSO and applied by spotting to the glass surface which had been treated to expose amide groups. After the spotting, the biochip was put in an oven at a temperature of 60° C. and a humidity of 40% and incubated for 1 hour, followed by a post-processing with succinic anhydride. The post-processing is to prevent a non-specific reaction of an unreacted amino group on the glass surface, epoxy group of a star-like PEG derivative having an epoxy group and amino group of a probe.

Figure 3:
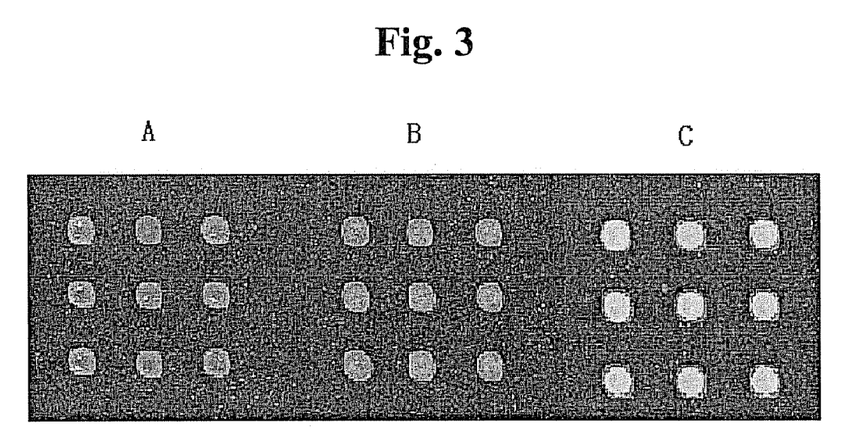
FIG. 3 is a photograph showing the result of fluorescent scanning performed after hybridization of a target nucleotide to a biochip manufactured in Example 6 according to the present invention.

On the resultant biochip, a hybridization reaction between the probe and a target nucleotide was performed. The result of scanning the chip surface is shown in FIG. 3. Here, the target nucleotide used was an artificial oligonucleotide complementary to the probe. In FIG. 3, "C" is for the biochip manufactured in this example, "B" is for the biochip manufactured in Example 4, and "A" is for a biochip manufactured by spotting only a DNA solution on a glass substrate. As is apparent from FIG. 3, the biochip "C" showed a fluorescent intensity 5-7 times greater than the biochip "B", and the biochip "A" showed a fluorescent intensity 2-3 times greater than the biochip "B".

As described above, according to the present invention, a 3D biochip having a structure where it spatially protrudes from its surface can be manufactured, and chip sensitivity is greatly increased. In addition, the biochip according to the present invention can be conveniently and efficiently manufactured using an aqueous solution at low costs.

What is claimed is:

1. A method for manufacturing a hydrogel microarray, comprising:
    mixing a polyethylene glycol having an epoxy group at its terminal and branches in 3 or more directions, a hydrophilic polymeric cross-linking agent which is a polyethylene glycol, and a probe in an aqueous solution to form a mixture solution; and
    applying the mixture solution on a substrate to form a hydrogel microarray such that the probe is immobilized to the substrate.

2. The method of claim 1, wherein the mixing comprises
    mixing the polyethylene glycol having an epoxy group at its terminal and branches in 3 or more directions and the hydrophilic polymeric cross-linking agent to form a matrix solution; and
    adding the probe in an aqueous solution to the matrix solution to form the mixture solution.

3. The method of claim 1, wherein the applying of the mixture solution on a substrate is performed at a temperature of about 40-70° C. and a humidity of about 60-30%.

4. The method of claim 1, wherein the hydrophilic polymeric cross-linking agent has an average molecular weight of about 60 to about 100,000 daltons.

5. The method of claim 1, wherein the probe comprises at least one of a deoxyribonucleic acid (DNA), a ribonucleic acid (RNA), a peptide nucleic acid (PNA), a protein, or an oligopeptide.

6. The method of claim 1, flirt her comprising treating a surface of the substrate to expose an amino group before applying the mixture solution on a substrate.

7. The method of claim 1, wherein the substrate is formed of a material selected from the group consisting of glass, quartz, silicon, plastic, polypropylene, polycarbonate, and activated acrylamide.

8. The method of claim 1, wherein the hydrophilic polymeric cross-linking agent comprises a functional group selected from the group consisting of a hydroxy group, an amino group, and a thiol group.

9. The method of claim 2, wherein the mixture solution comprises a matrix-probe conjugate.

10. The method of claim 4, further comprising treating a surface of the substrate to expose an amino group before applying the mixture solution on a substrate.

11. An assay method for detecting binding between a probe and a target substance, comprising:
    applying a sample comprising a target substance to a hydrogel microarray, wherein the hydrogel microarray is manufactured by the method of claim 1; and
    detecting the bound target substance.

12. The assay method of claim 11, wherein the target substance comprises a fluorescently-labeled biomolecule.

13. The assay method of claim 12, wherein the fluorescenctly-labeled biomolecule comprises an oligonucleotide.

* * * * *